United States Patent
Begley

(12) 
(10) Patent No.: US 6,201,125 B1
(45) Date of Patent: Mar. 13, 2001

(54) COMPOUNDS AND SYNTHESIS PROCESS

(75) Inventor: William J. Begley, Webster, NY (US)

(73) Assignee: Eastman Kodak Company, Rochester, NY (US)

( * ) Notice: Subject to any disclaimer, the term of this patent is extended or adjusted under 35 U.S.C. 154(b) by 0 days.

(21) Appl. No.: 09/473,636

(22) Filed: Dec. 28, 1999

(51) Int. Cl.$^7$ .................... C07D 213/81; C07D 263/56
(52) U.S. Cl. .................... 546/298; 546/323; 548/217
(58) Field of Search .................. 546/298, 323; 548/217

(56) References Cited

U.S. PATENT DOCUMENTS

| | | | |
|---|---|---|---|
| 4,533,625 | * 8/1985 | Ichijima et al. | 430/552 |
| 4,609,619 | 9/1986 | Katoh et al. | 430/553 |
| 4,775,616 | 10/1988 | Kilminster et al. | 430/552 |
| 4,849,328 | 7/1989 | Hoke et al. | 430/553 |
| 5,008,180 | 4/1991 | Merkel et al. | 430/552 |
| 5,045,442 | 9/1991 | Hoke | 430/553 |
| 5,145,483 | * 9/1992 | Junino et al. | 8/412 |
| 5,183,729 | 2/1993 | Naito et al. | 430/385 |
| 5,261,926 | * 11/1993 | Lang et al. | 8/406 |
| 5,378,596 | 1/1995 | Naruse et al. | 430/549 |
| 5,681,690 | 10/1997 | Tang et al. | 430/553 |
| 5,686,235 | 11/1997 | Lau et al. | 430/553 |

FOREIGN PATENT DOCUMENTS

59/111645   6/1984   (JP).

OTHER PUBLICATIONS

Aoki, Chemical Abstracts, 89:199093, 1978.*
Konishiroku Photo Industry Co., Chemical Abstracts, 99:222295, 1983.*
Monbaliu et al., Chemical Abstracts, 102:70034, 1985.*
JO 2035–450–A—Konica—Abstract—Feb. 6, 1990.
JO 1253–742–A—Konica—Abstract—Oct. 11, 1989.
JP 04163448–A—Konica—Abstract—Jun. 9, 1992.
JP 04212152–A—Fuji—Abstract—Aug. 3, 1992.
J5 9111 –645–A—Konishiroku –Abstract, Jun. 27, 1984.
"Heterocycles," 27(4), 881, (1988) by Mitsunori Ono.

* cited by examiner

Primary Examiner—Fiona T. Powers
(74) Attorney, Agent, or Firm—Arthur E. Kluegel

(57) ABSTRACT

Disclosed is a process for preparing 2,5-dicarbonamido phenol compounds comprising a step employing a 2-alkyl-6-nitro-benzoxazole to form a 2-alkyl-6-amino-benzoxazole in which the 2-alkyl group is unbranched at the $\alpha$ carbon. It also provides intermediate compounds useful in the process. The process provides a simple and safe way to prepare 2,5-dicarbonamido phenol compounds in good yield.

15 Claims, No Drawings

COMPOUNDS AND SYNTHESIS PROCESS

FIELD OF THE INVENTION

This invention relates to phenolic compounds bearing two amino substituents and a process for synthesizing such compounds using a 2-alkyl-6-nitro-benzoxazole to form a 2-alkyl-6-amino-benzoxazole in which the 2-alkyl group is unbranched at the α carbon.

BACKGROUND OF THE INVENTION

Phenolic compounds are useful for the synthesis of useful organic compounds such as couplers for colorant uses. Useful compounds include those having a substituted first amino group in the 2-position and a substituted second amino group in another position such as the 5-position of the phenol. One example of such useful compounds is a phenolic coupler useful as a cyan dye-forming coupler in a silver halide imaging process. To obtain the desired hue, they contain the requisite two amino groups including a ballast in one of the two groups. A ballast is a hydrophobic group having 8 or more aliphatic carbon atoms which serves to keep the coupler and resulting dye within the hydrophobic dispersion in which it is present so that it will not be washed out during the aqueous processes associated with development.

There have been available two processes for obtaining the desired phenol compounds. In the first, a phenol is provided with an amine group in the two position and a nitro group in the other desired amino position. The 2-position is converted to the desired amino substituent using acid chloride. Then, the nitro group is reduced to amine and the second amine group is converted to the desired amino substituent using acid chloride. It would be desirable to avoid it use of nitroaminophenol compounds for safety reasons since such materials present an explosion concern. Further, this method is limited in the order of introducing the substituents to the molecule.

Another method is described by Mitsunori Ono in "Heterocycles", 27(4), 881, (1988). The use of 2-alkyl-6-nitrobenzoxazoles is suggested to prepare the desired 2,5-dicarbonamido phenols. The examples employ a 2-t-butyl group, and it was found that an attempt to hydrolyze the oxazole ring in acid to deblock the 2-position was unsatisfactory and "all attempted usual acid cleavage . . . failed." Ono is ultimately concerned with effecting a reaction at the 4-position of the phenol ring rather than effecting a conversion of the nitro group, so the use of alkaline KOH hydrolysis is of no concern. But if one does desire to convert the nitro group, as in the present case, there is a major concern, because the use of alkaline KOH deblocking will also initiate undesired side reactions at the converted nitro site.

It is desirable to develop a process that provides a simple and safe way to prepare 2,5-dicarbonamido phenol compounds in good yield.

SUMMARY OF THE INVENTION

The invention provides a process for synthesizing 2,5-dicarbonamido phenol compounds comprising a step employing a 2-alkyl-6-nitro-benzoxazole to form a 2-alkyl-6-amino-benzoxazole in which the 2-alkyl group is unbranched at the α carbon. It also provides intermediate compounds useful in the process.

The process and intermediates provide a simple and safe way to prepare 2,5-dicarbonamido phenol compounds in good yield.

DETAILED DESCRIPTION OF THE INVENTION

The process of the invention is generally as described above. It is a process for synthesizing 2,5-dicarbonamido phenol compounds comprising a step employing a 2-alkyl-6-nitro-benzoxazole to form a 2-alkyl-6-amino-benzoxazole in which the 2-alkyl group is unbranched at the α carbon.

The starting 2-alkyl-5-chloro-benzoxazole material is readily available from The Aldrich Chemical Company of Milwaukee Wis., or can be made from 2-aminophenol upon reaction with a suitable acylating agent. The process entails nitrating the starting material to form a 2-alkyl-5-chloro-6-nitrobenzoxazole. The next step is to reduce the nitro group to the amine using any known method such as hydrogen plus a transition metal catalyst like Raney nickel. The resulting amine is then reacted to replace one of the amine hydrogen atoms such as by reaction with an acid chloride, including an alkyl, aryl or heterocyclic acid chloride. Appended reaction sites on the resulting carbonamide group may undergo further reactions such as the reaction of an electrophile or nucleophile.

Next, the oxazole is deblocked through acid hydrolysis to convert the compound into a 2-amino-5-carbonamidophenol. Now the 2-amino group is reacted with an acid chloride in the same manner as for the 5-position (but usually a different acid chloride compound is used.) The end result is the desired dicarbonamido phenol.

The scheme of the invention is exemplified in the following to prepare Compounds 8 and 13:

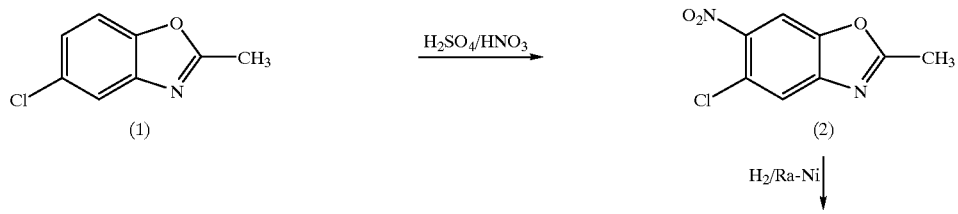

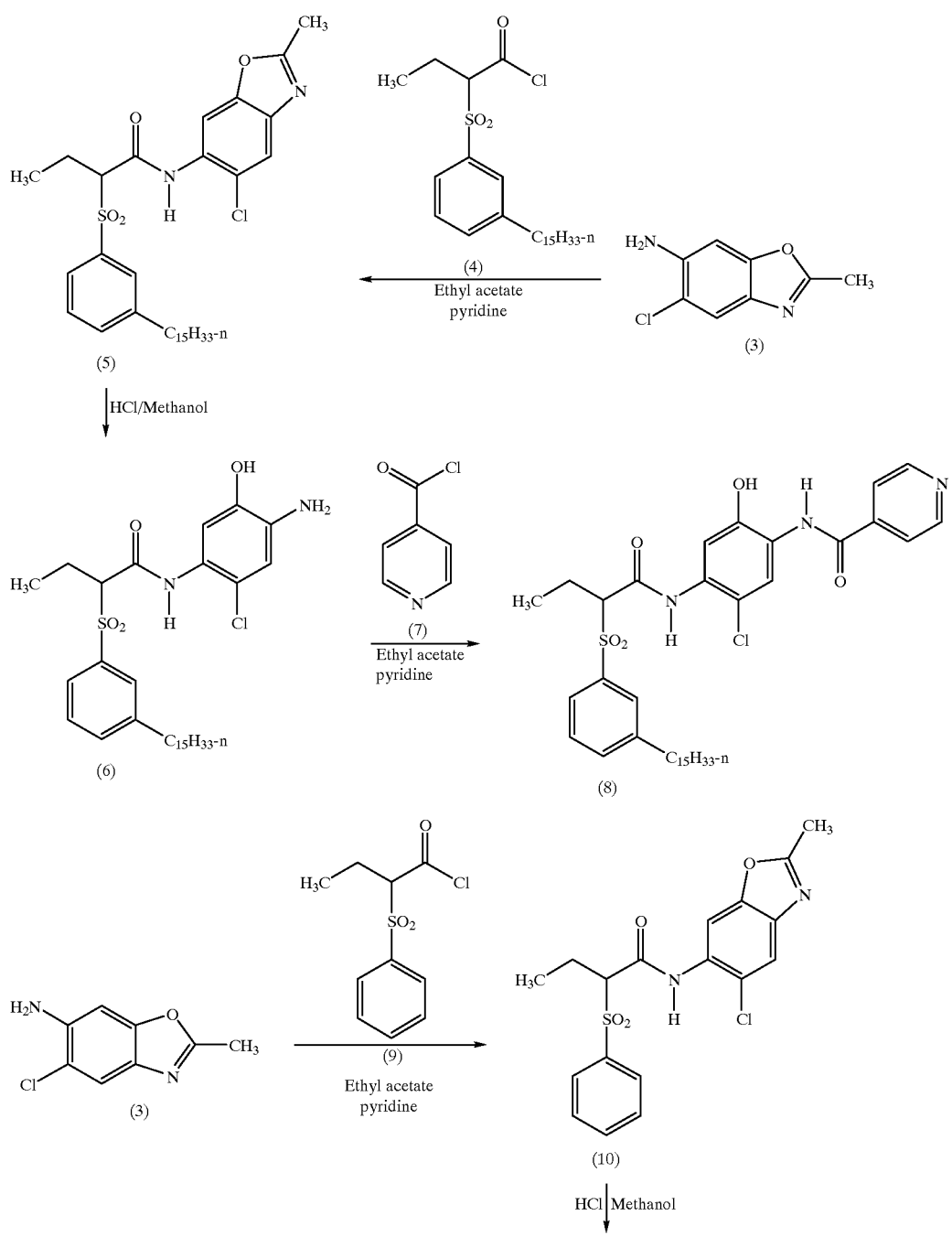

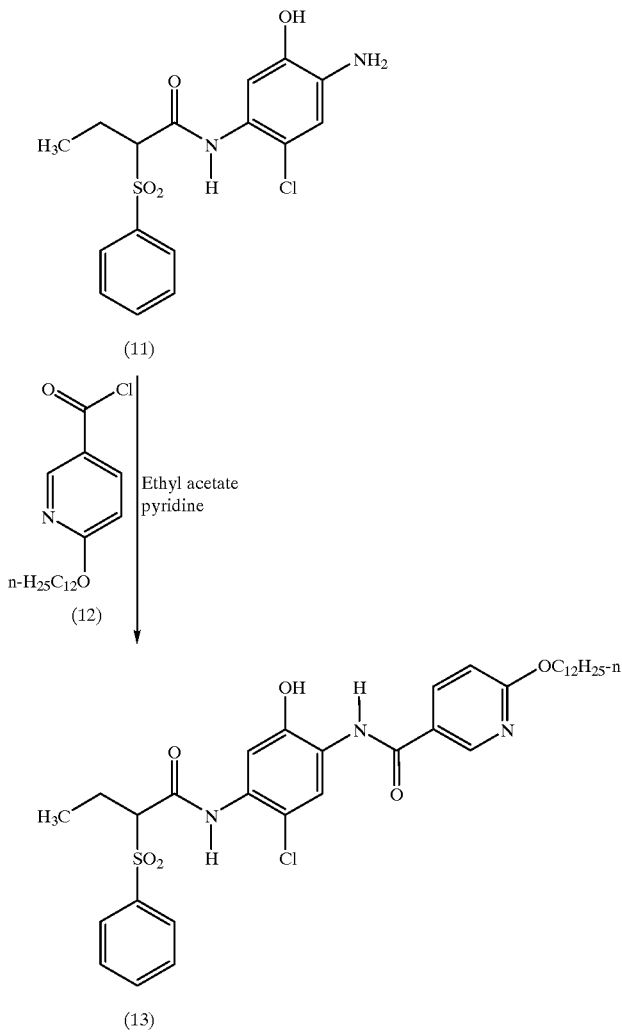

(11)

(12)

(13)

5-Chloro-2-methyl-6-nitrobenzoxazole (2)

Concentrated sulfuric acid (150 mL) was stirred mechanically and cooled in an ice/water bath. To this was gradually added 5-chloro-2-methylbenzoxazole (1), (75 g, 0.45 Moles), at such a rate that the temperature stayed at 30° C., over a 15–20 minute period. A solution of concentrated sulfuric acid (40 mL), and concentrated nitric acid (32 mL), was prepared and added drop by drop to the benzoxazole solution at such a rate that the temperature was maintained at approximately 20° C. When this acid solution had been added the cooling bath was removed and the mixture allowed to stir at room temperature for 1 hour. At the end of this period the solution was carefully poured onto ice with good stirring. Sufficient water was then added to get good mixing. The solid was filtered off, washed well with water followed by methanol and finally air dried. Yield 90.6 g

6-Amino-5-Chloro-2-methylbenzoxazole (3)

Compound (2), (30 g), was dissolved in tetrahydrofuran (150 mL), and Raney-Nickel which had been pre-washed with water (×3) and tetrahydrofuran (×3), was added. The mixture was then hydrogenated at room temperature and 50 psi of hydrogen. The reaction is complete in approximately 1.5 hours. After this period, the catalyst is filtered off and the solution concentrated under reduced pressure. The residue is triturated with heptane, cooled and the solid filtered off. Yield 22 g.

2-[(3-Pentadecylphenyl)sulfonyl]butanoyl chloride, (4).

2-[(3-Pentadecylphenyl)sulfonyl]butanoic acid (84.6 g, 0.193 Mole) was suspended in ethyl acetate (700 mL) to which was added dimethylformamide (0.5 mL) and thionyl chloride (70 mL, 0.964 Mole). The mixture was heated at 70° C. for 1.5 hours, cooled, concentrated under reduced pressure, co-evaporated with ethyl acetate (2×100 mL) and the oil so obtained used as such in the next step of the reaction sequence.

Compound (5).

6-Amino-5-Chloro-2-methylbenzoxazole (3), (32.0 g, 0.175 Mole) was dissolved in ethyl acetate (500 mL) with dry pyridine (15.6 mL, 0.193 Mole). The 2-[(3-pentadecylphenyl)sulfonyl]butanoyl chloride, (4), (0.193 Mole) dissolved in ethyl acetate (200 mL)was then added to the solution at a fairly fast drip rate over a 15 minute period while maintaining good stirring and keeping the temperature below 30° C. At the end of the addition, the cooling bath was removed and the reaction mixture stirred at room temperature for an additional 15 minutes. The reaction mixture was then washed with 2N-HCl (3×200 mL), dried (MgSO$_4$), filtered and concentrated to an oil. This oil was then taken on to the next step.

Compound (6).

Compound (5), (0.175 Mole) was dissolved in methanol (800 mL) and concentrated hydrochloric acid (40 mL)

added. The mixture was heated to 70° C. and after about 10 minutes complete dissolution of the initially precipitated material was achieved. After 1 hour a further volume of concentrated hydrochloric acid (20 mL) was added followed by 2 additional volumes (20 mL each) at 30 minute intervals. After the last volume had been added, the solution was heated for 30 more minutes, cooled and concentrated under reduced pressure until the product began to crystallize. Diethyl ether (1.0 L) was added and the mixture cooled overnight to 0° C. Following morning the product was filtered off, washed with diethyl ether and air dried. Yield 100 g.

4-Pyridinecarbonyl chloride, (7).

Isonicotinic acid (1.27 g, 10.36 mMole) was added to thionyl chloride (30 mL) and the mixture heated to 70° C. Alter 1 hour the solution was cooled, concentrated under reduced pressure and co-evaporated with ethyl acetate (2×30 mL). The residue was used as such in the following step.

Compound (8).

Compound (6) (5.0 g, 8.63 mMole), was suspended in ethyl acetate (50 mL), heated to 70° C. with good stirring and 4-pyridinecarbonyl chloride (7), (10.36 mMole) in ethyl acetate (10 mL) added drop by drop over a 15–20 minute period. The reaction mixture was then cooled, diluted with ethyl acetate washed with 2N-HCl(2×50 mL), dried (MgSO$_4$), filtered and concentrated under reduced pressure. The residue was dissolved in 50% ethyl acetate-heptane and subjected to flask chromatography eluting with 50% 60% and finally 70% ethyl acetate-heptane to obtain the product coupler, Inventive Compound (8). Yield 3.5 g.

2-(Phenylsulfonyl)butanoyl chloride, (9).

2-(Phenylsulfonyl)butanoic acid (41.2 g, 0.18 Mole) was suspended in ethyl acetate (250 mL) to which was added dimethylformamide (0.5 mL) and thionyl chloride (66 mL, 0.9 Mole). The mixture was heated at 70° C. for 1.5 hours, cooled, concentrated under reduced pressure, co-evaporated with ethyl acetate (2×100 mL) and the oil so obtained used as such in the next step of the reaction sequence.

Compound (10).

6-Amino-5-Chloro-2-methylbenzoxazole (3), (30.0 g, 0.1 6 Mole) was dissolved in ethyl acetate (250 mL) with dry pyridine (14.6 mL, 0.18 Mole). The 2-(phenyl)sulfonyl] butanoyl chloride, (9), (0.18 Mole) dissolved in ethyl acetate (100 mL)was then added to the solution at a fairly fast drip rate over a 15 minute period while maintaining good stirring and keeping the temperature below 30° C. At the end of the addition, the cooling bath was removed and the reaction mixture stirred at room temperature for an additional 15 minutes. The reaction mixture was then washed with 2N-HCl (3×200 mL), dried (MgSO$_4$), filtered and concentrated to an oil. This oil was then taken on to the next step.

Compound (11).

Compound (10), (0.18 Mole) was dissolved in methanol (400 mL) and concentrated hydrochloric acid (50 mL) added. The mixture was heated to 70° C. After 1 hour a further volume of concentrated hydrochloric acid (50 mL) was added followed by 1 additional volume (50 mL) at 30 minute intervals. After the last volume had been added, the solution was heated for 30 more minutes, cooled and concentrated under reduced pressure until the product began to crystallize. Diethyl ether (1.0 L) was added and the mixture cooled overnight to 0° C. Following morning the product was filtered off, washed with diethyl ether and air dried. Yield 50.7 g.

6-Dodecyloxy-3-pyridinecarbonyl chloride,(12).

6-Dodecyloxynicotinic acid (5.0 g, 16.26 mMole) was added to thionyl chloride (40 mL). Dimethylformamide (0.2 mL) was added and the mixture heated to 60° C. for 1 hour. The solution was then cooled, concentrated under reduced pressure and co-evaporated with ethyl acetate (3×40 mL). The residue was used in the next step of the sequence without further purification.

Compound (13).

The HCl salt of compound (11), (6.0 g, 14.78 mMole), was suspended in dry tetrahydrofuran (70 mL), heated to 70° C. and triethylamine (2.3 mL, 16.32 mMole) added. This mixture was then stirred for 10–15 minutes at this temperature. The 6-dodecyloxy-3-pyriclinecarbonyl chloride,(12), (16.26 mMole) in ethyl acetate (20 mL) was then added drop by drop with good stirring. The resulting mixture was then heated at 70° C. for a further 1 hour. The mixture was then cooled, diluted with ethyl acetate, washed with 2N-HCl (3×50 mL), dried (MgSO$_4$), filtered and concentrated under reduced pressure. The residue was dissolved in 30% ethyl acetate-heptane and subjected to flash chromatography eluting with the same solvent mixture followed by 40% ethyl acetate-heptane to collect the product, Compound (13). Yield 6.0 g.

Unless otherwise specifically stated, use of the term "substituted" or "substituent" means any group or atom other than hydrogen. Additionally, when the term "group" is used, it means that when a substituent group contains a substitutable hydrogen, it is also intended to encompass not only the substituent's unsubstituted form, but also its form further substituted with any substituent group or groups as herein mentioned, so long as the substituent does not destroy properties necessary for photographic utility. Suitably, a substituent group may be halogen or may be bonded to the remainder of the molecule by an atom of carbon, silicon, oxygen, nitrogen, phosphorous, or sulfur. The substituent may be, for example, halogen, such as chlorine, bromine or fluorine; nitro; hydroxyl; cyano; carboxyl; or groups which may be further substituted, such as alkyl, including straight or branched chain or cyclic alkyl, such as methyl, trifluoromethyl, ethyl, t-butyl, 3-(2,4-di-t-pentylphenoxy) propyl, and tetradecyl; alkenyl, such as ethylene, 2-butene; alkoxy, such as methoxy, ethoxy, propoxy, butoxy, 2-methoxyethoxy, sec-butoxy, hexyloxy, 2-ethylhexyloxy, tetradecyloxy, 2-(2,4-di-t-pentylphenoxy)ethoxy, and 2-dodecyloxyethoxy; aryl such as phenyl, 4-t-butylphenyl, 2,4,6-trimethylphenyl, naphthyl; aryloxy, such as phenoxy, 2-methylphenoxy, alpha- or beta-naphthyloxy, and 4-tolyloxy; carbonamido, such as acetamido, benzamido, butyramido, tetradecanamido, alpha-(2,4-di-t-pentyl-phenoxy)acetamido, alpha-(2,4-di-t-pentylphenoxy) butyramido, alpha-(3-pentadecylphenoxy)-hexanamido, alpha-(4-hydroxy-3-t-butylphenoxy)-tetradecanamido, 2-oxo-pyrrolidin-1-yl, 2-oxo-5-tetradecylpyrrolin-1-yl, N-methyltetradecanamido, N-succinimido, N-phthalimido, 2,5-dioxo-1-oxazolidinyl, 3-dodecyl-2,5-dioxo-1-imidazolyl, and N-acetyl-N-dodecylamino, ethoxycarbonylamino, phenoxycarbonylamino, benzyloxycarbonylamino, hexadecyloxycarbonylamino, 2,4-di-t-butylphenoxycarbonylamino, phenylcarbonylamino, 2,5-(di-t-pentylphenyl) carbonylamino, p-dodecyl-phenylcarbonylamino, p-tolylcarbonylamino, N-methylureido, N,N-dimethylureido, N-methyl-N-dodecylureido, N-hexadecylureido, N,N-dioctadecylureido, N,N-dioctyl-N'-ethylureido, N-phenylureido, N,N-diphenylureido, N-phenyl-N-p-tolylureido, N-(m-hexadecylphenyl)ureido, N,N-(2,5-di-t-pentylphenyl)-N'-ethylureido, and t-butylcarbonamido; sulfonamido, such as methylsulfonamido, benzenesulfonamido, p-tolylsulfonamido, p-dodecylbenzenesulfonamido, N-methyltetradecylsulfonamido, N,N-dipropylsulfamoylamino, and hexadecylsulfonamido; sulfamoyl, such as N-methylsulfamoyl, N-ethylsulfamoyl, N,N-dipropylsulfamoyl, N-hexadecylsulfamoyl, N,N-dimethylsulfamoyl; N-[3-(dodecyloxy)propyl]sulfamoyl, N-[4-(2,4-di-t-pentylphenoxy)butyl]sulfamoyl, N-methyl-N-tetradecylsulfamoyl, and N-dodecylsulfamoyl; carbamoyl, such as N-methylcarbamoyl, N,N-dibutylcarbamoyl, N-octadecylcarbamoyl, N-[4-(2,4-di-t-pentylphenoxy)butyl]carbamoyl, N-methyl-N-tetradecylcarbamoyl, and N,N-dioctylcarbamoyl; acyl, such as acetyl, (2,4-di-t-amylphenoxy)acetyl, phenoxycarbonyl, p-dodecyloxyphenoxycarbonyl methoxycarbonyl, butoxycarbonyl, tetradecyloxycarbonyl, ethoxycarbonyl, benzyloxycarbonyl, 3-pentadecyloxycarbonyl, and dodecyloxycarbonyl; sulfonyl, such asmethoxysulfonyl, octyloxysulfonyl, tetradecyloxysulfonyl, 2-ethylhexyloxysulfonyl, phenoxysulfonyl, 2,4-di-t-pentylphenoxysulfonyl, methylsulfonyl, octylsulfonyl, 2-ethylhexylsulfonyl, dodecylsulfonyl, hexadecylsulfonyl, phenylsulfonyl, 4-nonylphenylsulfonyl, and p-tolylsulfonyl; sulfonyloxy, such as dodecylsulfonyloxy, and hexadecylsulfonyloxy; sulfinyl, such as methylsulfinyl, octylsulfinyl, 2-ethylhexylsulfinyl, dodecylsulfinyl, hexadecylsulfinyl, phenylsulfinyl, 4-nonylphenylsulfinyl, and p-tolylsulfinyl; thio, such as ethylthio, octylthio, benzylthio, tetradecylthio, 2-(2,4-di-t-pentylphenoxy)ethylthio, phenylthio, 2-butoxy-5-t-octylphenylthio, and p-tolylthio; acyloxy, such as acetyloxy, benzoyloxy, octadecanoyloxy, p-dodecylamidobenzoyloxy, N-phenylcarbamoyloxy, N-ethylcarbamoyloxy, and cyclohexylcarbonyloxy; amine, such as phenylanilino, 2-chloroanilino, diethylamine, dodecylamine; imino, such as 1-(N-phenylimido)ethyl, N-succinimido or 3-benzylhydantoinyl; phosphate, such as dimethylphosphate and ethylbutylphosphate; phosphite, such as diethyl and dihexylphosphite; a heterocyclic group, a heterocyclic oxy group or a heterocyclic thio group, each of which may be substituted and which contain a 3 to 7 membered heterocyclic ring composed of carbon atoms and at least one hetero atom selected from the group consisting of oxygen, nitrogen and sulfur, such as 2-furyl, 2-thienyl, 2-benzimidazolyloxy or 2-benzothiazolyl; quaternary ammonium, such as triethylammonium; and silyloxy, such as trimethylsilyloxy.

If desired, the substituents may themselves be further substituted one or more times with the described substituent groups. The particular substituents used may be selected by those skilled in the art to attain the desired photographic properties for a specific application and can include, for example, hydrophobic groups, solubilizing groups, blocking groups, and releasing or releasable groups. When a molecule may have two or more substituents, the substituents may be joined together to form a ring such as a fused ring unless otherwise provided. Generally, the above groups and substituents thereof may include those having up to 48 carbon atoms, typically 1 to 36 carbon atoms and usually less than 24 carbon atoms, but greater numbers are possible depending on the particular substituents selected.

The materials of the invention can be used in any of the ways and in any of the combinations known in the art. Typically, the invention materials are incorporated in a melt and coated as a layer described herein on a support to form part of a photographic element. When the term "associated" is employed, it signifies that a reactive compound is in or adjacent to a specified layer where, during processing, it is capable of reacting with other components.

To control the migration of various components, it may be desirable to include a high molecular weight hydrophobe or "ballast" group in coupler molecules. Representative ballast groups include substituted or unsubstituted alkyl or aryl groups containing 8 to 48 carbon atoms. Representative substituents on such groups include alkyl, aryl, alkoxy, aryloxy, alkylthio, hydroxy, halogen, alkoxycarbonyl, aryloxcarbonyl, carboxy, acyl, acyloxy, amino, anilino, carbonamido, carbamoyl, alkylsulfonyl, arylsulfonyl, sulfonamido, and sulfamoyl groups wherein the substituents typically contain 1 to 42 carbon atoms. Such substituents can also be further substituted.

The entire contents of the patents and other publications referred to in this specification are incorporated herein by reference.

What is claimed is:

1. A process for preparing a 2,5-dicarbonamido phenol compound comprising reducing a 2-alkyl-6-nitro-benzoxazole to form a 2-alkyl-6-amino-benzoxazole in which the 2-alkyl group is unbranched at the α carbon.

2. The process of claim 1 in which the 2-alkyl-6-amino-benzoxazole is formed by reducing a 2-alkyl-6-nitrobenzoxazole.

3. The process of claim 2 in which the reduction is accomplished using hydrogen in the presence of a transition metal catalyst.

4. The process of claim 3 in which the reduction is accomplished using hydrogen in the presence of a nickel catalyst.

5. The process of claim 1 wherein the alkyl group is a normal alkyl group.

6. The process of claim 5 wherein the alkyl group is a methyl group.

7. The process of claim 1 comprising the further subsequent step of reacting the 6-amino group with an acid chloride in the presence of a base to convert the first amine to an amino carbonyl substituent.

8. The process of claim 5 comprising the further subsequent step of subjecting the 2-alkyl-6-amino-benzoxazole to acid hydrolysis to deblock the phenol in the presence of an acid to form a second amine substituent in the 2-position of the phenol.

9. The process of claim 8 comprising the still further subsequent step of reacting the second amine group with an acid chloride in the presence of a base to convert the second amine to an amino carbonyl substituent.

10. A 2-alkyl-6-aminobenzoxazole compound.

11. The compound of claim 10 in which the 2-alkyl group is unbranched at the α carbon.

12. The compound of claim 11 wherein the alkyl group is a normal alkyl group.

13. The compound of claim 12 wherein the alkyl group is a methyl group.

14. The compound of claim 10 comprising a carbonylamino group in the 6-position of the benzoxazole ring.

15. The compound of claim 14 wherein the carbonylamino group is a phenylsulfonylmethylcarbonamido group.

* * * * *